US006755792B2

(12) United States Patent
Masuda et al.

(10) Patent No.: US 6,755,792 B2
(45) Date of Patent: Jun. 29, 2004

(54) ARTERIOSCLEROSIS EXAMINING APPARATUS

(75) Inventors: Hiroshi Masuda, Komaki (JP); Toshihiko Ogura, Komaki (JP); Takashi Honda, Komaki (JP); Akira Tampo, Komaki (JP); Kiyoyuki Narimatsu, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 54 days.

(21) Appl. No.: 10/180,340

(22) Filed: Jun. 27, 2002

(65) Prior Publication Data

US 2003/0114764 A1 Jun. 19, 2003

(30) Foreign Application Priority Data

Dec. 17, 2001 (JP) ........................................ 2001-382550

(51) Int. Cl.[7] ................................................. A61B 5/00
(52) U.S. Cl. ........................................ 600/500; 600/485
(58) Field of Search ............................ 600/490, 493–6, 600/500–3, 485

(56) References Cited

U.S. PATENT DOCUMENTS

| 5,000,188 | A | * | 3/1991 | Kojima ....................... 600/500 |
| 5,582,179 | A | * | 12/1996 | Shimizu et al. ............. 600/500 |
| 5,961,467 | A | * | 10/1999 | Shimazu et al. ............ 600/485 |
| 6,355,000 | B1 | | 3/2002 | Ogura |
| 6,379,309 | B1 | | 4/2002 | Ogura et al. |
| 6,394,958 | B1 | * | 5/2002 | Bratteli et al. ............. 600/485 |
| 6,517,493 | B2 | * | 2/2003 | Ogura et al. ................ 600/490 |
| 6,524,257 | B2 | * | 2/2003 | Ogura ........................ 600/490 |

FOREIGN PATENT DOCUMENTS

| JP | 3027750 | 1/2000 |
| JP | B2 3140007 | 12/2000 |

* cited by examiner

*Primary Examiner*—Robert L. Nasser
(74) *Attorney, Agent, or Firm*—Oliff & Berridge, PLC

(57) ABSTRACT

An apparatus for examining arteriosclerosis of a living subject, including a pulse-wave detecting device which detects a pulse wave from a first portion of the subject, a stenosis-related-information obtaining device for obtaining, based on a shape of the pulse wave detected by the pulse-wave detecting device, stenosis-related information that changes in relation with stenosis of an artery of a second portion of the subject that is located upstream of the first portion of the subject in a direction in which blood flows in the artery, and a stenosis judging device for making, based on the stenosis-related information obtained by the stenosis-related-information obtaining device, a judgment about the stenosis of the artery of the second portion of the subject.

5 Claims, 10 Drawing Sheets

ARTERIOSCLEROSIS EXAMINING APPARATUS

BACKGROUND OF THE INVENTION

1. Field of the Invention

The present invention relates to an arteriosclerosis examining apparatus for examining arteriosclerosis, in particular, arteriosclerosis obliterans.

2. Related Art Statement

There is known, as a sort of arteriosclerosis, atherosclerosis that is arterial atheroma caused by deposit of lipid, such as cholesterol, on inner walls of arteries. Since atherosclerosis causes stenosis of arteries, it is also called arteriostenosis, or arteriosclerosis obliterans. There is known an inferior-and-superior-limb blood-pressure-index measuring apparatus as an apparatus for examining arteriostenosis. This apparatus is disclosed in, e.g., Japanese Patent No. 3,140,007 or its corresponding U.S. Pat. No. 6,355,000. The blood-pressure-index measuring apparatus includes two inflatable cuffs that are adapted to be worn on an inferior limb and a superior limb of a living subject, calculates, as an inferior-and-superior-limb blood-pressure index, a ratio of one of a superior-limb blood pressure and an inferior-limb blood pressure to the other, and examines arteriostenosis based on the thus calculated inferior-and-superior-limb blood-pressure index.

More specifically described, examination of arteriostenosis based on inferior-and-superior-limb blood-pressure index is effected by comparing the index value with a predetermined reference value. For example, in the case where an inferior-and-superior-limb blood-pressure index is calculated by dividing an inferior-limb systolic blood pressure by a superior-limb systolic blood pressure, if the index value is greater than 0.9, it can be judged that the subject does not have arteriostenosis and, if not, it can be judged that the subject is suspected of having arteriostenosis.

In many cases, arteriostenosis occurs to inferior limbs of living persons. Hence, the inferior-and-superior-limb blood-pressure-index measuring apparatus is used for the purpose of examining arteriostenosis of inferior limbs. In fact, arteriostenosis may occur to other regions of living persons. However, the examination based on the inferior-and-superior-limb blood-pressure index cannot be used to diagnose or identify in which region arteriostenosis is present.

SUMMARY OF THE INVENTION

It is therefore an object of the present invention to provide an arteriosclerosis examining apparatus which can accurately examine arteriosclerosis of a living subject.

The above object has been achieved by the present invention. According to a first aspect of the present invention, there is provided an apparatus for examining arteriosclerosis of a living subject, comprising a pulse-wave detecting device which detects a pulse wave from a first portion of the subject; a stenosis-related-information obtaining means for obtaining, based on a shape of the pulse wave detected by the pulse-wave detecting device, stenosis-related information that changes in relation with stenosis of an artery of a second portion of the subject that is located upstream of the first portion of the subject in a direction in which blood flows in the artery; and a stenosis judging means for making, based on the stenosis-related information obtained by the stenosis-related-information obtaining means, a judgment about the stenosis of the artery of the second portion of the subject.

If the artery located upstream of the portion where the pulse-wave detecting device is worn has stenosis, the shape of the pulse wave detected by the detecting device changes in relation with the stenosis. Therefore, the stenosis-related-information obtaining means obtains, based on the shape of the pulse wave detected by the pulse-wave detecting device, the stenosis-related information that changes in relation with the stenosis, and the stenosis judging means makes, based on the stenosis-related information obtained, a judgment about the stenosis of the artery located upstream of the portion where the detecting device is worn. Thus, the present apparatus may be used such that the pulse-wave detecting device is worn on each one of different portions of the subject so as to make a judgment about stenosis of an artery located upstream of the each portion, or may employ a plurality of pulse-wave detecting devices which are adapted to be worn on different portions of the subject so as to detect respective pulse waves and make, based on those pulse waves, respective judgments about stenosis of respective arteries located upstream of those portions. In either case, the present apparatus can identify an arteriostenotic portion of the subject.

A waveform of the pulse wave detected by the pulse-wave detecting device may be deformed by noise such as arrhythmia or physical motion of the subject. This pulse wave is not appropriate for use in making a diagnosis on arteriostenosis. If stenosis-related information is obtained based on the inappropriate pulse wave, an appropriate diagnosis cannot be made on arteriostenosis.

Hence, preferably, the stenosis-related-information obtaining means comprises means for selecting, from a plurality of heartbeat-synchronous pulses of the pulse wave detected by the pulse-wave detecting device, at least one heartbeat-synchronous pulse whose waveform has an identifiable characteristic point; and means for obtaining the stenosis-related information based on the selected heartbeat-synchronous pulse.

According to this feature, the stenosis-related-information obtaining means selects, from the heartbeat-synchronous pulses of the pulse wave detected by the pulse-wave detecting device, a heartbeat-synchronous pulse whose waveform has an identifiable characteristic point, and the stenosis-related information is obtained based on the thus selected heartbeat-synchronous pulse. The stenosis-related information obtained based on the heartbeat-synchronous pulse whose waveform has the identifiable characteristic point is accurate information, and the stenosis judging means makes, based on the accurate stenosis-related information, a judgment about the stenosis of the artery located upstream of the portion where the detecting device is worn. Thus, the present apparatus can make an accurate diagnosis about arteriostenosis.

According to another feature of the first aspect, the stenosis-related-information obtaining means comprises a sharpness-degree determining means for determining a degree of sharpness of each of a plurality of heartbeat-synchronous pulses of the pulse wave detected by the pulse-wave detecting device; and an average-sharpness-degree calculating means for calculating an average of the respective degrees of sharpness of the heartbeat-synchronous pulses of the pulse wave determined by the sharpness-degree determining means, and the stenosis judging means makes the judgment about the stenosis of the artery of the second portion of the subject, based on a degree of sharpness of at least one heartbeat-synchronous pulse of the pulse wave determined by the sharpness-degree determining means, when a comparison value which is obtained by comparing the degree of sharpness of the at least one heartbeat-synchronous pulse, with the average sharpness degree calculated by the average-sharpness-degree calculating means, falls within a reference range.

According to this feature, the stenosis judging means makes the judgment about the stenosis of the artery, based on an average one of respective degrees of sharpness of respective heartbeat-synchronous pulses of the pulse wave detected by the pulse-wave detecting device. It can be said that an average degree of sharpness is derived from a heartbeat-synchronous pulse whose waveform is not deformed by noise or arrhthmia. Thus, the present apparatus can make an accurate diagnosis about the stenosis of the artery located upstream of the portion where the detecting device is worn.

According to a second aspect of the present invention, there is provided an apparatus for examining arteriosclerosis of a living subject, comprising a first-pulse-wave detecting device which detects, as a first pulse wave, a pulse wave from a first portion of the subject; a second-pulse-wave detecting device which detects, as a second pulse wave, the pulse wave from a second portion of the subject that is different from the first portion of the subject; a stenosis-related-information obtaining means for obtaining, based on a shape of the first pulse wave detected by the first-pulse-wave detecting device, first stenosis-related information that changes in relation with stenosis of a first artery of a third portion of the subject that is located upstream of the first portion of the subject in a direction in which blood flows in the first artery, and obtaining, based on a shape of the second pulse wave detected by the second-pulse-wave detecting device, second stenosis-related information that changes in relation with stenosis of a second artery of a fourth portion of the subject that is located upstream of the second portion of the subject in a direction in which blood flows in the second artery; and a stenosis judging means for making, based on the first stenosis-related information, and the second stenosis-related information, obtained by the stenosis-related-information obtaining means, a judgment about the stenosis of the first artery of the second portion of the subject, a judgment about the stenosis of the second artery of the fourth portion of the subject, and a judgment about a stenosis of a third, common artery that is located upstream of the first and second arteries in a direction in which blood flows in the third artery.

According to this aspect, the stenosis-related-information obtaining means obtains, based on the shape of the first pulse wave detected by the first-pulse-wave detecting device, the first stenosis-related information, and obtains, based on the shape of the second pulse wave detected by the second-pulse-wave detecting device, the second stenosis-related information. The first stenosis-related information reflects the stenosis of the first artery located upstream of the portion where the first-pulse-wave detecting device is worn, and the second stenosis-related information reflects the stenosis of the second artery located upstream of the portion where the second-pulse-wave detecting device is worn. Therefore, if the subject has arteriostenosis in a portion located upstream of the junction of the first and second arteries, both the first and second stenosis-related information values indicate arteriostenosis; if the subject has arteriostenosis in the first artery located downstream of the junction, only the first stenosis-related information value indicates arteriostenosis; and if the subject has arteriostenosis in the second artery located downstream of the junction, only the second stenosis-related information value indicates arteriostenosis. Thus, the stenosis judging means can make, based on the first stenosis-related information and the second stenosis-related information, a judgment about a stenosis of an artery located upstream of the junction of the first and second arteries, a judgment about the stenosis of the first artery located downstream of the junction, and a judgment about the stenosis of the second artery located downstream of the junction.

According to a preferred feature of the second aspect, the arteriosclerosis examining apparatus further comprises a pulse-wave-propagation-velocity-related-information obtaining device which obtains, based on the first pulse wave detected by the first-pulse-wave detecting device, first pulse-wave-propagation-velocity-related information that is related to a first velocity at which the pulse wave propagates in a fourth artery of the subject that includes the first artery of the third portion of the subject that is located upstream of the first portion of the subject.

Since pulse-wave propagation velocity lowers in an artery located downstream of an arteriostenotic portion, the length of the artery in which the velocity lowers increases as the distance of the stenotic portion from the portion where the first pulse wave is detected increases. Therefore, the amount of change of the pulse-wave-propagation-velocity-related information obtained by the pulse-wave-propagation-velocity-related-information obtaining device increases as the stenotic portion goes upstream along the artery from which the information is obtained. Thus, the stenotic portion can be identified based on the pulse-wave-propagation-velocity-related information obtained by the pulse-wave-propagation-velocity-related-information obtaining device.

According to the first aspect of the present invention, the stenosis judging means automatically makes a judgment about stenosis of an artery located upstream of the portion where the pulse-wave detecting device is worn. However, if the pulse wave detected by the pulse-wave detecting device is displayed by a display device, a medical person can make, to some extent, a judgment about arteriostenosis, based on the pulse wave displayed. However, as described above, the pulse-wave detecting device may detect an inappropriate pulse wave whose waveform is deformed by noise such as arrhythmia or physical motion of the subject. Based on the inappropriate pulse wave, an appropriate diagnosis cannot be made on arteriostenosis.

According to a fourth aspect of the present invention, there is provided an apparatus for examination of arteriosclerosis of a living subject, comprising a pulse-wave detecting device which detects, from a portion of the subject, a pulse wave including a plurality of heartbeat-synchronous pulses; a display device which displays a waveform of at least one heartbeat-synchronous pulse of the pulse wave detected by the pulse-wave detecting device; and a pulse-wave displaying means for operating the displaying device to display the waveform of the at least one heartbeat-synchronous pulse of the pulse wave when the waveform of the at least one heartbeat-synchronous pulse has an identifiable characteristic point.

According to this aspect, the pulse-wave displaying means operates the displaying device to display the waveform of the heartbeat-synchronous pulse of the pulse wave when the waveform of the heartbeat-synchronous pulse has an identifiable characteristic point. It can be said that a pulse wave whose waveform has an identifiable characteristic point is a pulse wave whose waveform is little deformed. Therefore, a medical person can make, based on the waveform of the pulse wave displayed by the display device, an accurate judgment about the stenosis of the artery located upstream of the portion where the pulse-wave detecting device is worn. The present apparatus may be used such that the pulse-wave detecting device is worn on each one of different portions of the subject so that the display device displays the pulse wave detected by the detecting device worn on the each portion and the medical person can make, based on the pulse wave displayed, a judgment about stenosis of an artery located upstream of the each portion, or may employ a plurality of pulse-wave detecting devices which are adapted to be worn on different portions of the subject so that the display device displays respective pulse waves detected by the detecting devices and the person can make, based on those pulse waves displayed, respective judgments about stenosis of respective arteries located upstream of those portions. In either case, the person can identify an arteriostenotic portion of the subject.

According to a fifth aspect of the present invention, there is provided an apparatus for examination of arteriosclerosis of a living subject, comprising a pulse-wave detecting device which detects, from a portion of the subject, a pulse wave including a plurality of heartbeat-synchronous pulses; a display device which displays a waveform of at least one heartbeat-synchronous pulse of the pulse wave detected by the pulse-wave detecting device; a sharpness-degree determining means for determining a degree of sharpness of each of the heartbeat-synchronous pulses of the pulse wave detected by the pulse-wave detecting device; an average-sharpness-degree calculating means for calculating an average of the respective degrees of sharpness of the heartbeat-synchronous pulses of the pulse wave determined by the sharpness-degree determining means; and a pulse-wave displaying means for operating, when a comparison value obtained by comparing a degree of sharpness of the at least one heartbeat-synchronous pulse of the pulse wave, determined by the sharpness-degree determining means, with the average sharpness degree calculated by the average-sharpness-degree calculating means, falls within a reference range, the display device to display the waveform of the at least one heartbeat-synchronous pulse of the pulse wave.

According to this aspect, the pulse-wave displaying means operates, when a comparison value obtained by comparing a degree of sharpness of a heartbeat-synchronous pulse of the pulse wave, determined by the sharpness-degree determining means, with the average sharpness degree calculated by the average-sharpness-degree calculating means, falls within a reference range, the display device to display a waveform of the heartbeat-synchronous pulse of the pulse wave. That is, the display device displays a waveform of a heartbeat-synchronous pulse having a near-average degree of sharpness. It can be said that a pulse wave having a near-average sharpness degree is a pulse wave whose waveform is not deformed by noise or arrhythmia. Therefore, a medical person can make, based on the waveform of the pulse wave displayed by the display device, an accurate judgment about the stenosis of the artery located upstream of the portion where the pulse-wave detecting device is worn. Like the apparatus according to the fourth aspect, the present apparatus can be used to detect respective pulse waves from different portions so that the medical person can make, based on those pulse waves, respective judgments about stenosis of respective arteries located upstream of those portions. That is, the medical person can identify an arteriostenotic portion of the subject.

In an exemplary embodiment, the pulse-wave-propagation-velocity-related-information obtaining device obtains, based on the second pulse wave detected by the second-pulse-wave detecting device, second pulse-wave-propagation-velocity-related information that is related to a second velocity at which the pulse wave propagates in a fifth artery of the subject that includes the second artery of the fourth portion of the subject that is located upstream of the second portion of the subject, and the apparatus includes a stenotic-portion identifying means for identifying, based on a comparison value obtained by comparing the first pulse-wave-propagation-velocity-related-information and the second pulse-wave-propagation-velocity-related information, with each other, a stenotic-portion of each of the first and second arteries.

BRIEF DESCRIPTION OF THE DRAWINGS

The above and optional objects, features, and advantages of the present invention will be better understood by reading the following detailed description of the preferred embodiments of the invention when considered in conjunction with the drawings, in which.

DETAILED DESCRIPTION OF PREFERRED EMBODIMENTS

Figure 1:
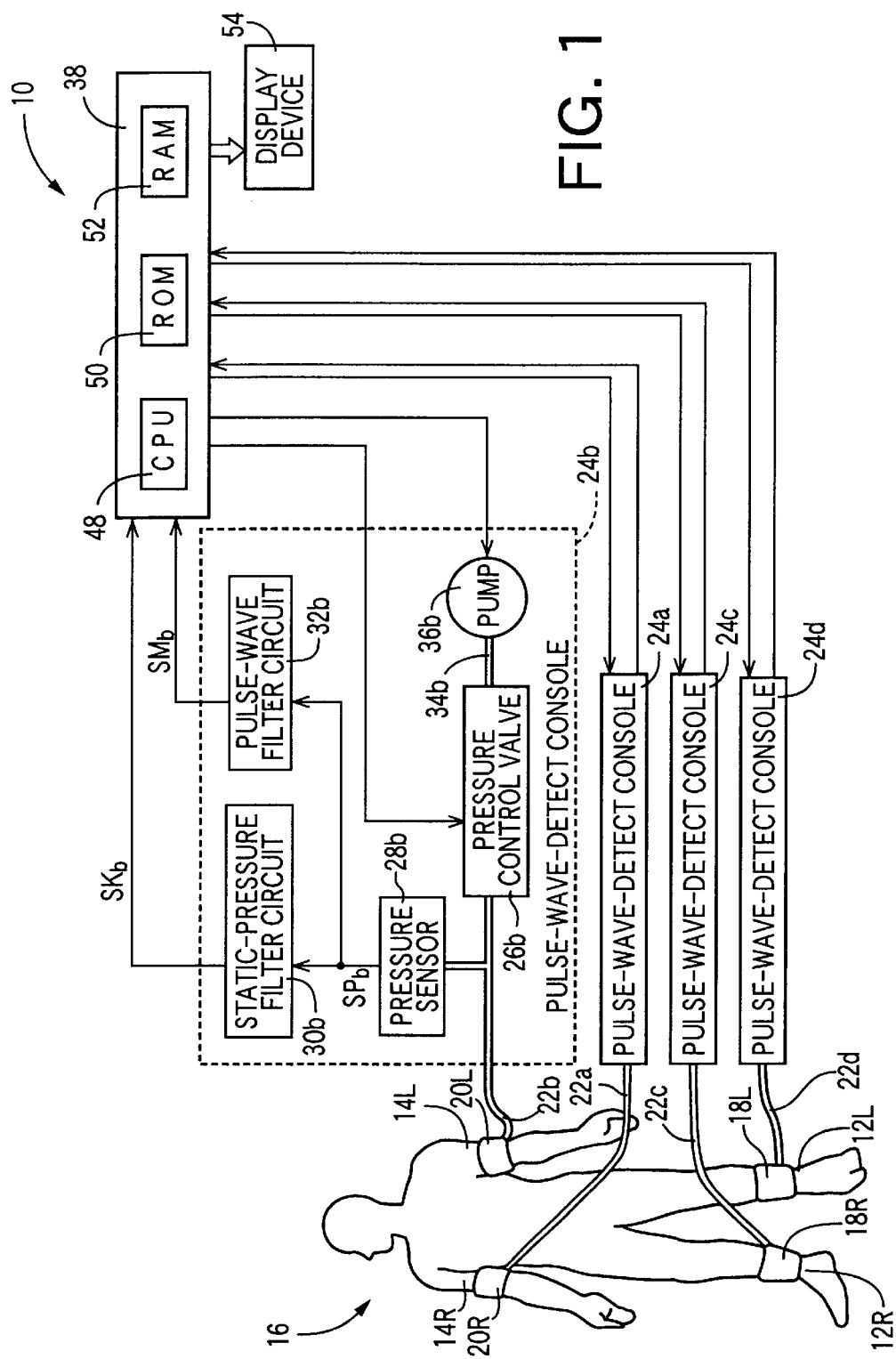
FIG. 1 is a diagrammatic view for explaining a construction of an arteriosclerosis examining apparatus to which the present invention is applied.

Hereinafter, there will be described in detail an embodiment of the present invention by reference to the drawings. FIG. 1 shows a diagrammatic view for explaining a construction of an arteriosclerosis examining apparatus 10 to which the present invention is applied.

In FIG. 1, the arteriosclerosis examining apparatus 10 includes a left ankle cuff 18L and a right ankle cuff 18R which are wound around a left ankle 12L and a right ankle 12R, respectively, of a patient 16, and a left upper-arm cuff 20L and a right upper-arm cuff 20R which are wound around a left upper arm 14L and a right upper arm 14R, respectively, of the patient 16. Each of the cuffs 18, 20 functions as a pressing band which presses a portion of the patient around which the each cuff is wound, and includes a belt-like outer bag which is formed of a non-stretchable material such as cloth or polyester; and a rubber bag accommodated in the outer bag.

The left and right upper-arm cuffs 20L, 20R are connected via respective pipings 22b, 22a to respective pulse-wave-detect consoles 24b, 24a; and the left and right ankle cuffs 18L, 18R are connected via respective pipings 22d, 22c to respective pulse-wave-detect consoles 24d, 24c.

Since the four pulse-wave-detect consoles 24a, 24b, 24c, 24d have an identical construction, the pulse-wave-detect console 24b to which the left upper-arm cuff 20L is connected will be described below as a representative of the four devices 24. The pulse-wave-detect console 24b includes a pressure control valve 26b, a pressure sensor 28b, a static-pressure filter circuit 30b, a pulse-wave filter circuit 32b, a piping 34b, and an air pump 36b, and the piping 22b is connected to the pressure control valve 26b and the pressure sensor 28b. The pressure control valve 26b is connected via the piping 34b to the air pump 36b.

The pressure control valve 26b controls a pressure of a pressurized air supplied from the air pump 36b, supplies the pressure-controlled air to the left upper-arm cuff 20L, and discharges the pressurized air from the left upper-arm cuff 20L, so as to control the air pressure in the cuff 20L.

The pressure sensor 28b detects the air pressure in the left upper-arm cuff 20L, and supplies a pressure signal, $SP_b$, representing the detected air pressure, to the static-pressure filter circuit 30b and the pulse-wave filter circuit 32b. The static-pressure filter circuit 30b includes a low-pass filter which extracts, from the pressure signal $SP_b$, a cuff-pressure signal, $SK_b$, representing a static component of the detected pressure, i.e., a pressing pressure of the cuff 20L (hereinafter, referred to as the left-upper-arm cuff pressure, $PC_b$). The filter circuit 30b supplies the cuff-pressure signal $SK_b$ to an electronic control device 38 via an A/D (analog-to-digital) converter, not shown.

The pulse-wave filter circuit 32b includes a band-pass filter which extracts, from the pressure signal $SP_b$, a left-upper-arm pulse-wave signal, $SM_b$, representing a left-upper-arm pulse wave $WB_L$ as an oscillatory component of the detected pressure that has prescribed frequencies. The filter circuit 32b supplies the pulse-wave signal $SM_b$ to the control device 38 via an A/D converter, not shown. Since the pulse-wave signal $SM_b$ represents the left-upper-arm pulse wave $WB_L$ produced from an artery of the left upper arm 14L pressed by the left upper-arm cuff 20L, the left upper-arm cuff 20L and the pulse-wave-detect console 24b cooperate with each other to function as a left-upper-arm-pulse-wave detecting device 40 (FIG. 2).

Similarly, a right-upper-arm pulse wave $WB_R$ is represented by a right-upper-arm pulse-wave signal $SM_a$ extracted by a pulse-wave filter circuit 32a, and accordingly the right upper-arm cuff 20R and the pulse-wave-detect console 24a cooperate with each other to function as a right-upper-arm-pulse-wave detecting device 42. Moreover, a left-ankle pulse wave $WA_L$ is represented by a left-ankle pulse-wave signal $SM_d$ extracted by a pulse-wave filter circuit 32d, and accordingly the left ankle cuff 18L and the pulse-wave-detect console 24d cooperate with each other to function as a left-ankle-pulse-wave detecting device 44. Similarly, a right-ankle pulse wave $WA_R$ is represented by a right-ankle pulse-wave signal $SM_c$ extracted by a pulse-wave filter circuit 32c, and accordingly the right ankle cuff 18R and the pulse-wave-detect console 24c cooperate with each other to function as a right-ankle-pulse-wave detecting device 46. Two pulse waves arbitrarily selected from the left-upper-arm pulse wave $WB_L$, the right-upper-arm pulse wave $WB_R$, the left-ankle pulse wave $WA_L$, and the right-ankle pulse wave $WA_R$ function as a first pulse wave and a second pulse wave, respectively; and two pulse-wave detecting devices out of the four devices 40, 42, 44, 46 that detect the first and second pulse waves, respectively, function as a first-pulse-wave detecting device and a second-pulse-wave detecting device, respectively.

The control device 38 is essentially provided by a microcomputer including a CPU (central processing unit) 48, a ROM (read only memory) 50, a RAM (random access memory) 52, and an I/O (input-and-output) port, not shown. The CPU 48 processes signals according to the control programs pre-stored in the ROM 50, while utilizing the temporary-storage function of the RAM 52, and the CPU 48 outputs, from the I/O port, drive signals to the respective air pumps 36 and respective pressure control valves 26 of the four pulse-wave-detect consoles 24, so as to control the respective operations of those elements 36, 26 and thereby control the respective pressures in the cuffs 18, 20. In addition, the CPU 48 processes the signals supplied to the control device 38 and thereby controls a display device 54 to display a pulse wave whose waveform is little deformed, and additionally makes a judgment about arteriostenosis of a portion located upstream of a portion where each one of the four cuffs 18, 20 is worn and thereby controls the display device 54 to display the judgments made and an arteriostenotic portion identified based on the judgments.

Figure 2:
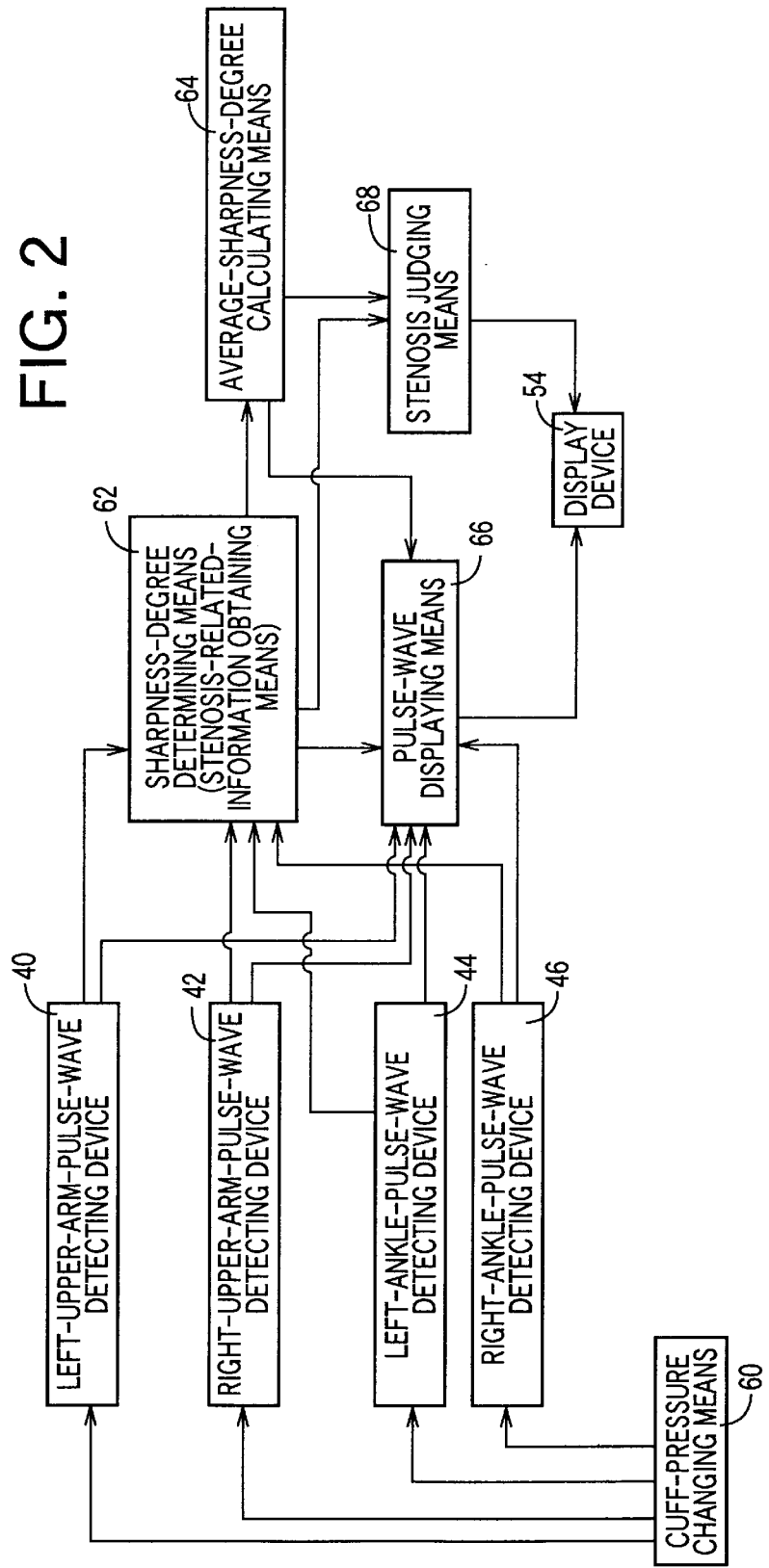
FIG. 2 is a diagrammatic view for explaining essential control functions of a CPU (central processing unit) of a control device, shown in FIG. 1.

FIG. 2 is a diagrammatic view for explaining essential control functions of the CPU 48. A cuff-pressure changing means 60 controls the respective air pumps 36a, 36b, 36c, 36d and respective pressure control valves 26a, 26b, 26c, 26d of the four pulse-wave detecting devices 40, 42, 44, 46, so as to control the respective cuff pressures $PC_a$, $PC_b$, $PC_c$, $PC_d$ to respective predetermined pulse-wave detecting pressures. The pulse-wave detecting pressures are predetermined at respective pressures which are lower than respective diastolic blood pressures of the respective portions where the cuffs 18, 20 are worn and which assure that the respective pulse-wave signals SM extracted by the respective pulse-wave filter circuits 32 have a sufficiently great magnitude, for example, are predetermined at 50 mmHg.

Figure 3:
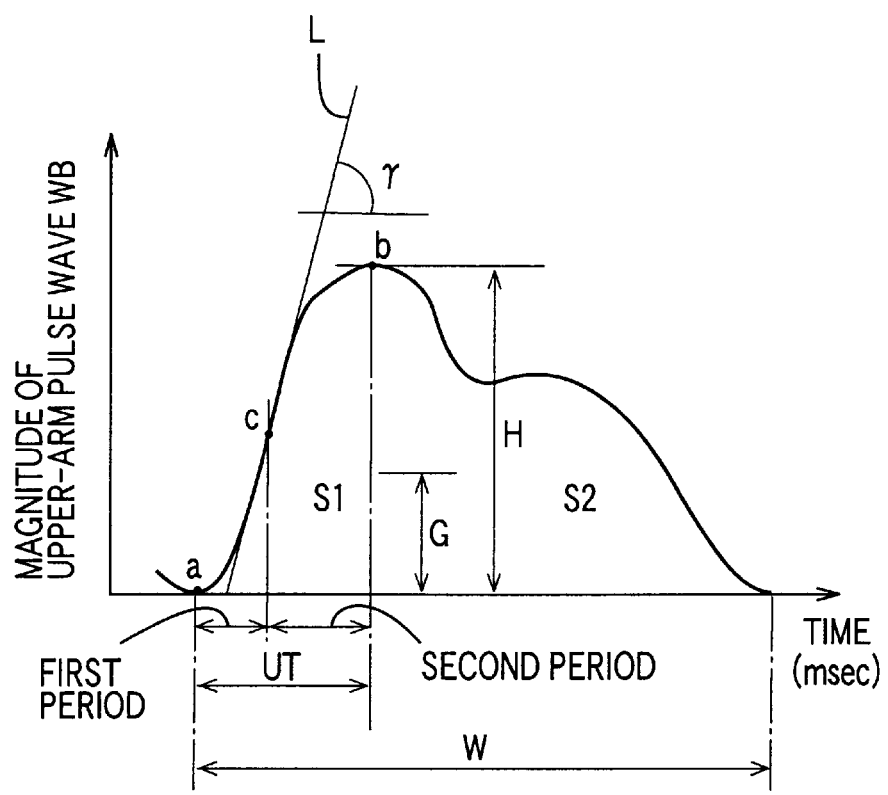
FIG. 3 is a graph showing an example of an upper-arm pulse wave WB.

A sharpness-degree determining means 62 determines a degree of sharpness of each of successive heartbeat-synchronous pulses of each of the respective pulse waves detected by the four pulse-wave detecting devices 40, 42, 44, 46 in a state in which the respective cuff pressures $PC_a$, $PC_b$, $PC_c$, $PC_d$ are maintained at the respective predetermined pulse-wave detecting pressures by the cuff-pressure changing means 60. A degree of sharpness of a pulse wave corresponds to a degree of upward projection of the pulse wave. The sharpness degree may be expressed as a normalized pulse area VR (=$S/(W \times H)$) which is obtained by dividing a pulse area S calculated by summarizing one heartbeat-synchronous pulse of, e.g., an upper-arm pulse wave WB shown in FIG. 3, over a pulse period W, by a product ($W \times H$) of a height H of a peak point b and the pulse period W; a normalized value of a first-half area S1 calculated by summarizing a first half portion from a rising point a to the peak point b; a normalized value of a second-half area S2 calculated by summarizing a second half portion following the peak point b; or a normalized value I/W obtained by dividing, by the pulse period W, a width I of one heartbeat-synchronous pulse at a height equal to two thirds, $H \times (\frac{2}{3})$, of the peak-point height H. The normalized pulse area VR may be expressed as a parameter % MAP (=$100 \times G/H$) that is a percentage of a height G of a center of gravity of the pulse area S relative to the peak-point height H, i.e., pulse pressure. If the patient has arteriostenosis in the portion located upstream of the portion where each one of the cuffs 18, 20 is worn, the degree of upward projection of heartbeat-synchronous pulse of the pulse wave detected by the each cuff 18, 20 lowers, and accordingly the parameter VR or % MAP increases. Thus, the sharpness degree functions as stenosis-related information, more specifically, waveform-characteristic information that changes in relation with arteriostenosis; and the sharpness-degree determining means 62 functions as a stenosis-related-information obtaining means. Respective sharpness degrees determined for the first and second pulse waves selected from the left-upper-arm pulse wave $WB_L$, the right-upper-arm pulse wave $WB_R$, the left-ankle pulse wave $WA_L$, and the right-ankle pulse wave $WA_R$, function as first stenosis-related information and second stenosis-related information, respectively.

An average-sharpness-degree calculating means 64 calculates an average of the respective sharpness degrees of the successive heartbeat-synchronous pulses of the left-upper-arm pulse wave $WB_L$, determined by the sharpness-degree determining means 62. Similarly, the average-sharpness-degree calculating means 64 calculates an average of the respective sharpness degrees of successive pulses of the right-upper-arm pulse wave $WB_R$, an average of the respective sharpness degrees of successive pulses of the left-ankle pulse wave $WA_L$, and an average of the respective sharpness degrees of successive pulses of the right-ankle pulse wave $WA_R$.

A pulse-wave displaying means 66 calculates a comparison value by comparing each of respective sharpness degrees of respective heartbeat-synchronous pulses of the left-upper-arm pulse wave $WB_L$, determined by the sharpness-degree determining means 62, with the average sharpness degree of the left-upper-arm pulse wave $WB_L$, calculated by the average-sharpness-degree calculating means 64, and, if the thus calculated comparison value falls within a predetermined range, the displaying means 66 operates the display device 54 to display a waveform of the corresponding pulse of the left-upper-arm pulse wave $WB_L$. Here, a comparison value indicates a degree of difference between each sharpness degree and an average sharpness degree, and may be a difference itself between the two degrees, or a ratio of one of the two degrees to the other. The fact that a comparison value falls within the predetermined range means that its corresponding sharpness degree is around the average sharpness degree. Therefore, the display device 54 displays only a waveform of a heartbeat-synchronous pulse of the left-upper-arm pulse wave $WB_L$ that is less influenced or deformed by incidental noise such as arrhythmia or physical motion of the patient. Similarly, regarding each one of the right-upper-arm pulse wave $WB_R$, the left-ankle pulse wave $WA_L$, and the right-ankle pulse wave $WA_R$, the displaying means 66 calculates a comparison value in the same manner as described above and, if the thus calculated comparison value falls within the predetermined range, operates the display device 54 to display a waveform of a heartbeat-synchronous pulse of the each pulse wave $WB_R$, $WA_L$, $WA_R$.

A stenosis judging means 68 judges, based on each of the sharpness degrees of the left-upper-arm pulse wave $WB_L$ determined by the sharpness-degree determining means 62, whether an "upstream" artery of a portion located upstream of the portion where the left upper-arm cuff 20L is worn has stenosis or not, or which degree of stenosis the upstream artery has. The sharpness degree increases as the degree of stenosis of the upstream artery increases. Therefore, if each sharpness degree determined from the left-upper-arm pulse wave $WB_L$ exceeds an upper limit of a predetermined normal range, then the stenosis judging means 68 judges that the artery located upstream of the left upper-arm cuff 20L has stenosis, and determines, based on an amount of excess of the each sharpness degree from the normal range, a degree of stenosis of the artery located upstream of the left upper-arm cuff 20L. Similarly, regarding each of the right-upper-arm pulse wave $WB_R$, the left-ankle pulse wave $WA_L$, and the right-ankle pulse wave $WA_R$, the judging means 68 judges, based on each of the sharpness degrees of the each pulse wave $WB_R$, $WA_L$, $WA_R$, determined by the sharpness-degree determining means 62, whether an "upstream" artery of a portion located upstream of the portion where the corresponding cuff 20R, 18L, 18R is worn has stenosis or not, or which degree of stenosis the upstream artery has. Here, it is preferred that the stenosis judging means 68 use only the sharpness degrees determined for the heartbeat-synchronous pulses whose waveforms are displayed on the display device 54 by the pulse-wave displaying means 66, that is, only the sharpness degrees corresponding to the comparison values falling within the predetermined range.

In addition, the stenosis judging means 68 identifies an arteriostenotic portion, based on the thus made four judgments about whether the respective arteries of the respective portions located upstream of the respective portions where the four cuff 20L, 20R, 18L, 18R are worn have stenosis or not, and a predetermined relationship between four judgments and arteriostenotic portion, pre-stored in the ROM 52, and operates the display device 54 to display the thus identified arteriostenotic portion of the patient.

Figure 4:
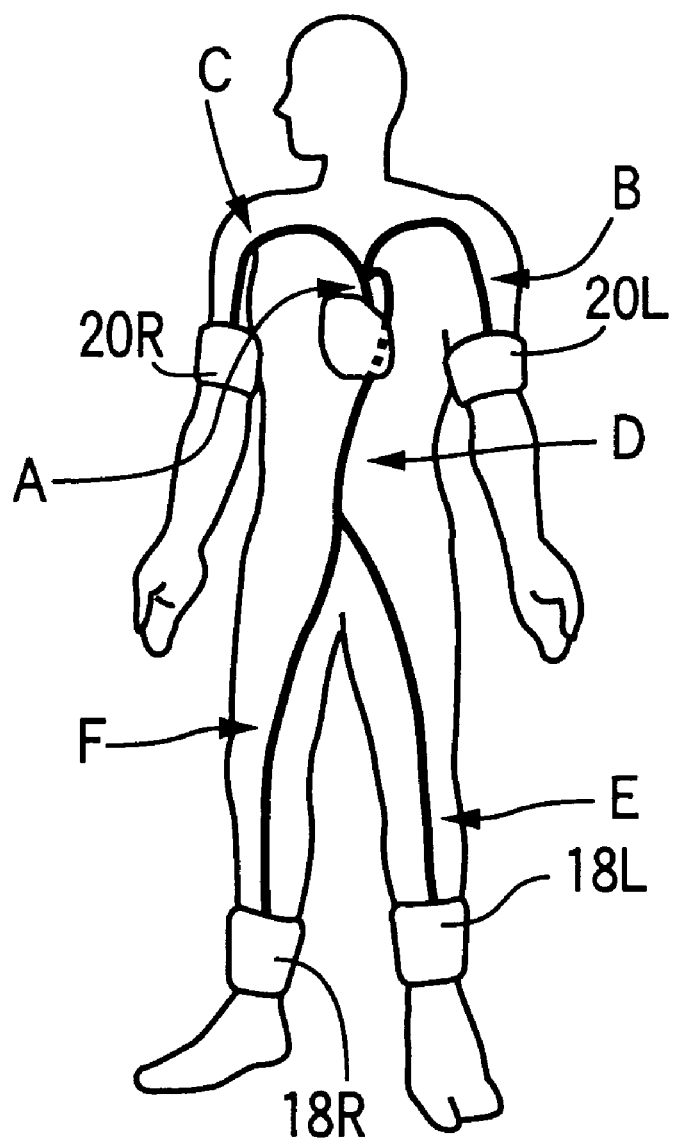
FIG. 4 is a view for explaining arteries A, B, C, D, E, and F.

Table 1 shows the pre-stored relationship between four judgments and arteriostenotic portion. In the following description of Table 1, it is assumed, for easier understanding purposes only, that the four pulse-wave detecting devices 40, 42, 44, 46 function as a third, a fourth, the first, and the second pulse-wave detecting device, respectively, and that the respective arteries of the respective portions located upstream of the respective portions where the four cuff 20L, 20R, 18L, 18R are worn are a third, a fourth, a first, and a second artery of the patient, respectively. However, since the first and second pulse-wave detecting devices can be arbitrarily selected from the four pulse-wave detecting devices 40, 42, 44, 46, as described above, the first and second arteries can also be arbitrarily selected from the four arteries located upstream of the four cuff 20L, 20R, 18L, 18R. In addition, it is assumed, as shown in FIG. 4, that an artery between the heart and a junction of the third and fourth arteries (hereinafter, referred to as the first junction) is an artery A; an artery between the first junction and the portion where the left-upper-arm cuff 20L is worn is an artery B; an artery between the first junction and the portion where the right-upper-arm cuff 20R is worn is an artery C; an artery between the first junction and a junction of the first and second arteries (hereinafter, referred to as the second junction) is an artery D; an artery between the second junction and the portion where the left-ankle cuff 18L is worn is an artery E; and an artery between the second junction and the portion where the right-ankle cuff 18R is worn is an artery F.

TABLE 1

| FIRST ARTERY | SECOND ARTERY | THIRD ARTERY | FOURTH ARTERY | STENOTIC PORTION |
|---|---|---|---|---|
| ○ | ○ | ○ | ○ | NONE |
| ○ | X | ○ | ○ | F |
| X | ○ | ○ | ○ | E |
| ○ | ○ | ○ | X | C |

TABLE 1-continued

| FIRST ARTERY | SECOND ARTERY | THIRD ARTERY | FOURTH ARTERY | STENOTIC PORTION |
|---|---|---|---|---|
| ◯ | ◯ | X | ◯ | B |
| X | X | ◯ | ◯ | D |
| X | X | X | X | A |

In Table 1, symbol "O" indicates presence of stenosis and symbol "X" indicates absence of stenosis. The relationship shown in Table 1 will be described in more detail below. For example, Line 3 of Table 1 shows that only the first artery has stenosis and, in this case, the stenosis judging means 68 judges that a portion of the first artery that is not common to the other arteries, i.e., the artery E is a stenotic portion. Line 6 of Table 1 shows that the first and second arteries have stenosis and the third and fourth arteries do not have stenosis and, in this case, the stenosis judging means 68 judges that a portion that is common to the first and second arteries and is not common to the third and fourth arteries, i.e., the artery D is a stenotic portion. Last line of Table 1 shows that all the arteries have stenosis and, in this case, the stenosis judging means 68 judges that a portion that is common to all the arteries, i.e., the artery A is a stenotic portion (e.g., aortic stenosis). Here, it is noted that Table 1 is prepared on the assumption that a living subject has a single stenotic portion.

Figure 5:
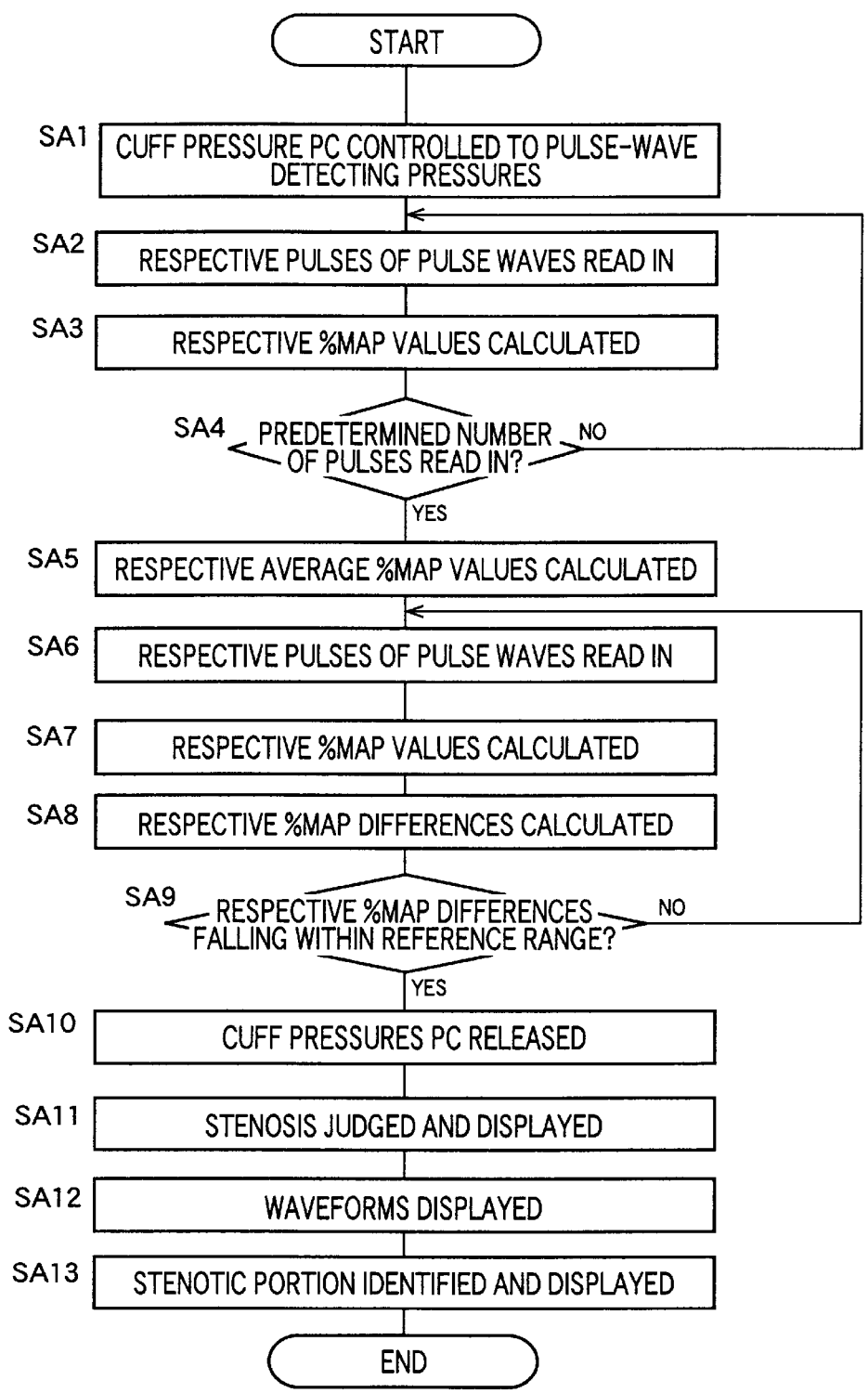
FIG. 5 is a flow chart representing the essential control functions of the CPU, shown in FIG. 2.

FIG. 5 is a flow chart representing the essential control functions of the CPU 48, shown in FIG. 2. First, at Step SA1 of FIG. 5 (hereinafter, the terms "Step(s)" are omitted), the CPU 48 controls the air pumps 36a, 36b, 36c, 36d and the pressure control valves 26a, 26b, 26c, 26d to change and maintain the cuff pressures $PC_a$, $PC_b$, $PC_c$, $PC_d$ to and at the above-described respective pulse-wave detecting pressures.

Then, at SA2, the CPU reads in one heartbeat-synchronous pulse of each of the respective pulse waves supplied from the four pulse-wave detecting devices 40, 42, 44, 46. Then, the control goes to SA3 corresponding to the sharpness-degree determining means 62. At SA3, the CPU determines a % MAP value of each of the respective heartbeat-synchronous pulses of the four pulse waves, read in at SA2. Then, the control goes to SA4 where the CPU judges whether the CPU has read in, at SA2, a predetermined number of (e.g., ten) heartbeat-synchronous pulses of each of the four pulse waves. If a negative judgment is made at SA4, the control goes back to SA2.

Meanwhile, if a positive judgment is made at SA4, then the control goes to SA5 corresponding to the average-sharpness-degree calculating means 64. At SA5, the CPU calculates an average of the respective % MAP values of the predetermined number of pulses of each of the four pulse waves, i.e., calculates respective average % MAP values of the four pulse waves. Then, the control goes to SA6 where the CPU again reads in one heartbeat-synchronous pulse of each of the respective pulse waves supplied from the four pulse-wave detecting devices 40, 42, 44, 46. Then, the control goes to SA7 corresponding to the sharpness-degree determining means 62. At SA7, the CPU determines a third % MAP value (i.e., third stenosis-related information) of the heartbeat-synchronous pulse of the left-upper-arm pulse wave $WB_L$, a fourth % MAP value (i.e., fourth stenosis-related information) of the heartbeat-synchronous pulse of the right-upper-arm pulse wave $WB_R$, a first % MAP value (i.e., first stenosis-related information) of the heartbeat-synchronous pulse of the left-ankle pulse wave $WA_L$, and a second % MAP value (i.e., second stenosis-related information) of the heartbeat-synchronous pulse of the right-ankle pulse wave $WA_R$.

Then, at SA8, the CPU calculates respective % MAP differences by subtracting, from the respective % MAP values of the four pulse waves, determined at SA7, the respective average % MAP values of the four pulse waves, calculated at SA5. Subsequently, the control goes to SA9 where the CPU judges whether each of the four % MAP differences, calculated at SA8, falls within a predetermined reference range whose middle value is equal to zero and which is considerably narrow. A positive judgment made at SA9 means that each of the % MAP values, determined at SA7, and a corresponding one of the average % MAP values, calculated at SA5, are close to each other, and additionally means that a shape of a corresponding one of the four heartbeat-synchronous pulses, read in at SA6, has little deformation and accordingly is suitable for use in making a diagnosis about arteriotenosis. Therefore, if a positive judgment is made at SA9, the control goes to SA10 and the following steps, without read in additional pulses of the four pulse waves. On the other hand, if a negative judgment is made at SA9, the control goes back to SA6.

At SA10, the CPU stops the air pumps 36a, 36b, 36c, 36d and controls the pressure control valves 26a, 26b, 26c, 26d to decrease the cuff pressures $PC_a$, $PC_b$, $PC_c$, $PC_d$ to an atmospheric pressure. In the present flow chart, SA1 and SA10 corresponding to the cuff-pressure changing means 60.

Then, at SA11, the CPU judges, based on the % MAP value of each one of the first to fourth pulse waves, determined at SA7, whether a corresponding one of the first to fourth arteries has stenosis. More specifically described, if the % MAP value of each one of the first to fourth pulse waves, determined at SA7, falls within a corresponding one of respective normal ranges predetermined for the four pulse waves, the CPU judges that one of the first to fourth arteries that corresponds to the each one pulse wave does not have stenosis; and if not, the CPU judges that the one artery has stenosis. Each one of the first to fourth pulse waves is detected from the downstream end of a corresponding one of the first to fourth arteries. In addition, the CPU operates the display device 54 to display the results of those judgments.

Figure 6:
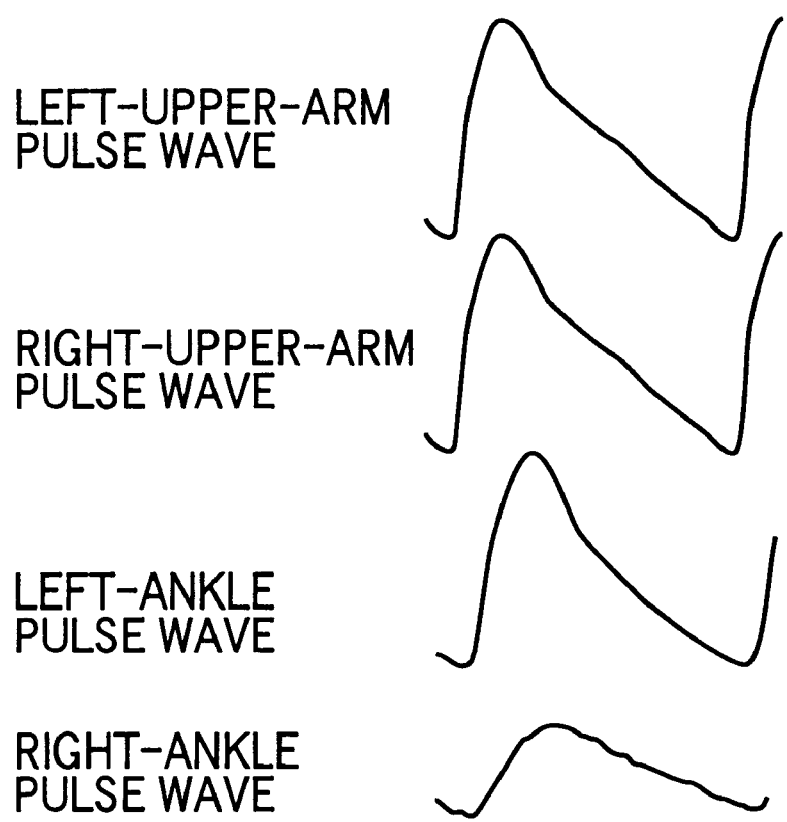
FIG. 6 is a graph showing respective examples of pulse waves displayed at Step SA12 of FIG. 5.

Then, at SA12, the CPU operates the display device 54 to display respective waveforms of the respective heartbeat-synchronous pulses of the four pulse waves, read in at SA6, that correspond to the respective % MAP differences for which the positive judgment had been made at SA9. FIG. 6 shows respective examples of the respective pulses of the four pulse waves, displayed at SA12. From FIG. 6, it can be understood that a sharpness degree of the pulse of the right-ankle pulse wave $WA_R$ only is low and, from this fact, it can be judged by a medical person that the right inferior limb has stenosis. In the flow chart of FIG. 5, SA9 and SA12 correspond to the pulse-wave displaying means 66.

Subsequently, at SA13, the CPU identifies a stenotic portion of the patient based on the presence or absence of stenosis in each of the first to fourth arteries, judged at SA11, and the relationship shown in Table 1, and operates the display device 54 to display the identified stenotic portion. In the flow chart of FIG. 5, SA11 and SA13 corresponds to the stenosis judging means 68.

In the embodiment employing the flow chart shown in FIG. 5, at SA7 (the sharpness-degree determining means 62), the CPU determines, based on the shape of the pulse waves detected by each of the pulse-wave detecting devices 40, 42, 44, 46, the % MAP value that changes in relation with stenosis of the artery located upstream of the portion where the each pulse-wave detecting device is worn. And, at SA11 and SA13 (the stenosis judging means 68), the CPU makes, based on the thus determined % MAP value, a judgment about the stenosis of the artery located upstream of the portion where the each pulse-wave detecting device 40, 42, 44, 46 is worn, and identifies the stenotic portion of the patient based on the presence or absence of stenosis of each of the four arteries.

In addition, in the embodiment employing the flow chart shown in FIG. 5, at SA11 (the stenosis judging means 68), the CPU selects, from the respective % MAP values determined for the respective heartbeat-synchronous pulses of each of the respective pulse waves detected by the four pulse-wave detecting devices 40, 42, 44, 46, one % MAP value that is close to the average % MAP value of the each pulse wave, and makes a judgment about arteriostenosis, based on the thus selected one % MAP value. Since the one % MAP value is close to the average % MAP value, it can be said that the one % MAP value has been determined from the heartbeat-synchronous pulse whose shape had not been deformed by noise or arrhythmia. Thus, the present apparatus can make an accurate diagnosis about the stenosis of the artery located upstream of the portion where the cuff 18, 20 is worn.

Moreover, in the embodiment employing the flow chart shown in FIG. 5, at SA7 (the sharpness-degree determining means 62), the CPU determines the first % MAP value based on the shape of the left-ankle pulse wave $WA_L$ detected by the left-ankle-pulse-wave detecting device 44, and the second % MAP value based on the shape of the right-ankle pulse wave $WA_R$ detected by the right-ankle-pulse-wave detecting device 46. The first % MAP value reflects the stenosis of the first artery, and the second % MAP value reflects the stenosis of the second artery. Therefore, if arteriostenosis occurs to the artery located upstream of the junction of the first and second arteries, that is, the artery A or D, both the first and second % MAP values indicate arteriostenosis; if arteriostenosis occurs to the first artery located downstream of the junction, i.e., the artery E, only the first % MAP value indicates arteriostenosis; and if arteriostenosis occurs to the second artery located downstream of the junction, i.e., the artery F, only the second % MAP value indicates arteriostenosis. Thus, at SA13 (the stenosis judging means 68), the CPU can make, based on the first and second % MAP values, a judgment about the stenosis of each of the arteries A, D, E, and F, according to the pre-stored relationship shown in Table 1.

In addition, in the embodiment employing the flow chart shown in FIG. 5, at SA12 (the pulse-wave displaying means 66), the CPU operates the display device 54 to display the respective waveforms of the respective heartbeat-synchronous pulses of the four pulse waves, detected by the pulse-wave detecting devices 40, 42, 44, 46, that correspond to the respective % MAP differences which are obtained by subtracting the respective average % MAP values from the respective % MAP values and which are judged as falling within the predetermined reference range. Thus, the display device 54 displays only the respective waveforms of the respective heartbeat-synchronous pulses whose % MAP values are close to the respective average % MAP values. Since those waveforms are free of noise or arrhythmia, a medical person can make an accurate diagnosis about the stenosis of each of the respective arteries located upstream of the cuffs 18, 20, based on the shape of a corresponding one of the waveforms. If the person make respective judgments about stenosis of the respective arteries located upstream of the respective portions where the four cuffs 18, 20 are worn, based on the four pulse waves displayed on the display device 54, the person can identify a stenotic portion of the patient based on those judgments.

Next, there will be described another embodiment of the present invention. The same reference numerals as used in the above-described embodiment are used to designate the corresponding elements of the present embodiment, and the description thereof is omitted.

Figure 7:
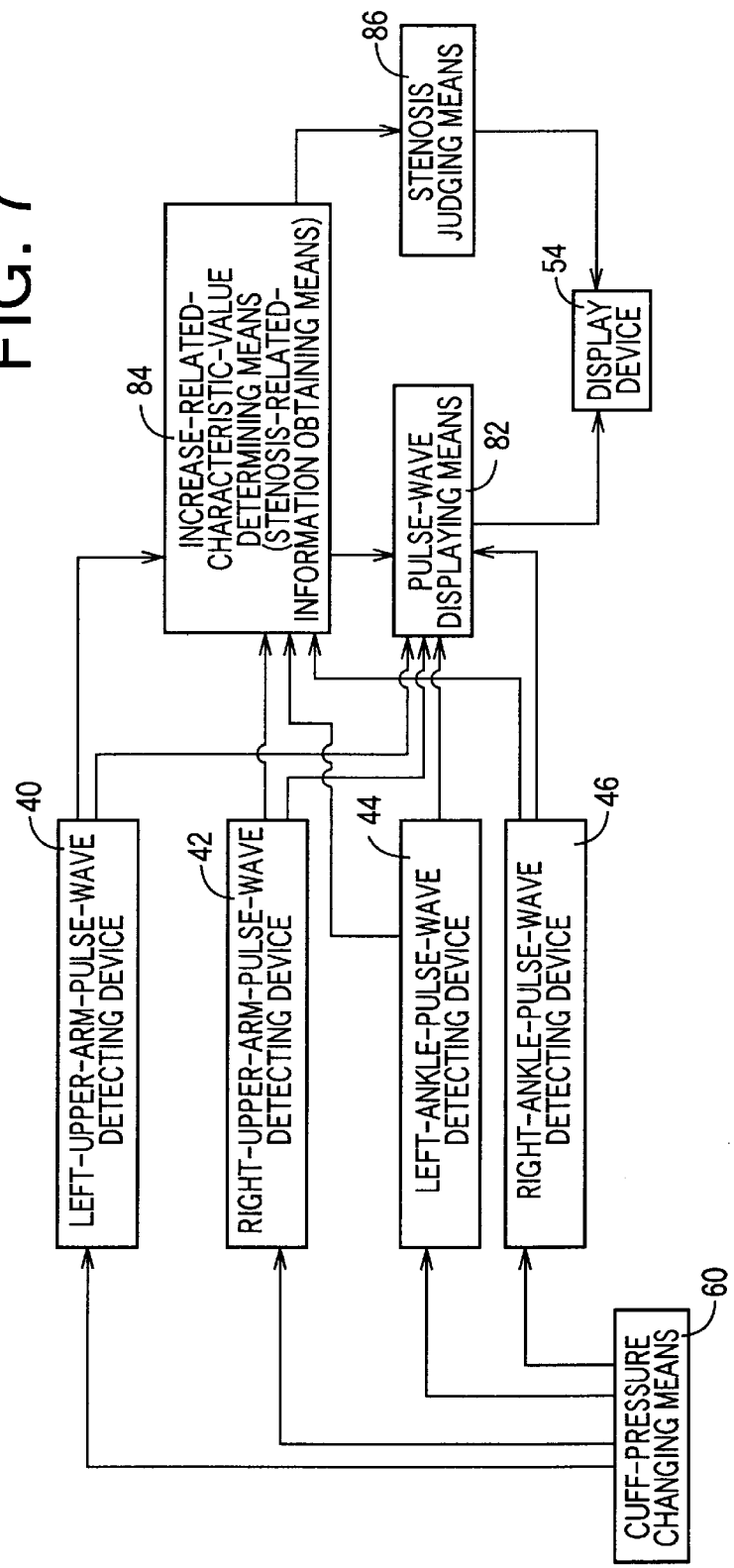
FIG. 7 is a diagrammatic view for explaining essential control functions of a CPU of a control device of another arteriosclerosis examining apparatus as a second embodiment of the present invention.

FIG. 7 shows essential control functions of a CPU 48 of another arteriosclerosis examining apparatus differing from the above-described apparatus 10. The present apparatus differs from the preceding apparatus 10 with respect to only some control functions of the CPU 48 employed in the present apparatus.

A pulse-wave displaying means 82 selects, from the respective heartbeat-synchronous pulses of each of the respective pulse waves detected by the four pulse-wave detecting devices 40, 42, 44, 46 in the state in which the respective cuff pressures $PC_a$, $PC_b$, $PC_c$, $PC_d$ are maintained at the respective pulse-wave detecting pressures by the cuff-pressure changing means 60, one or more heartbeat-synchronous pulses whose waveforms have a clear or identifiable characteristic point, and operates the display device 54 to display the waveforms of the thus selected heartbeat-synchronous pulses. A characteristic point is defined as a point characteristic of a normal heartbeat-synchronous pulse that is free of noise; such as a rising point or a peak point. Regarding an upper-arm pulse wave WB, in particular, the characteristic point thereof may be a dicrotic notch. When each pulse-wave signal SM is passed through a band-pass filter which selectively allows passing of only a signal component having frequencies corresponding to a characteristic point, and if an amplitude of the signal outputted by the band-pass filter is greater than a reference value, the displaying means 82 judges that the each pulse-wave signal SM represents a pulse wave whose waveform has a clear or identifiable characteristic point.

An increase-related-characteristic-value determining means 84 determines respective increase-related characteristic values of the respective heartbeat-synchronous pulses of the respective pulse waves detected by the four pulse-wave detecting devices 40, 42, 44, 46 in the state in which the respective cuff pressures $PC_a$, $PC_b$, $PC_c$, $PC_d$ are maintained at the respective pulse-wave detecting pressures by the cuff-pressure changing means 60. An increase-related characteristic value is defined as a value characteristic of an increasing portion of a heartbeat-synchronous pulse of a pulse wave (i.e., a portion between a rising point and a peak point of the pulse); such as those shown in FIG. 3. More specifically described, an increase-related characteristic value may be an upstroke time (UT) (msec) of a increasing portion of an upper-arm pulse wave WB between a rising point, a, and a peak point, b; the greatest slope, γ, that can be taken by a line L tangential to the increasing portion between the rising point a and the peak point b, i.e., a slope γ of the line L tangential to a point c of the increasing portion where the slope γ takes the greatest value; a first period of the increasing portion, defined by and between the rising point a and the greatest-slope point c; a second period of the increasing portion, defined by and between the greatest-slope point c and the peak point b; or a ratio of one of the first and second periods to the other. There is a tendency that as the degree of arteriostenosis increases, the slope of the increasing portion of the upper-arm pulse wave WB decreases. That is, the increase-related characteristic value changes in relation with arteriostenosis. For example, as the degree of arteriostenosis increases, the upstroke time UT increases. Thus, the increase-related characteristic value is a sort of stenosis-related pulse-wave information, and the increase-related-characteristic-value determining means 84 functions as stenosis-related-pulse-wave-information obtaining means. Here, it is preferred to determine respective increase-related characteristic values of the respective heartbeat-synchronous pulses whose waveforms have been judged as having a clear characteristic point by the pulse-wave displaying means 82.

A stenosis judging means 86 judges, based on each of the increase-related characteristic values of the left-upper-arm pulse wave $WB_L$ determined by the increase-related-characteristic-value determining means 62, whether an upstream artery of a portion located upstream of the portion where the left upper-arm cuff 20L is worn has stenosis or not, or which degree of stenosis the upstream artery has. As described above, the increase-related characteristic value changes in relation with the stenosis of the upstream artery. Therefore, if each increase-related characteristic value does not fall within a predetermined normal range, then the stenosis judging means 86 judges that the artery located upstream of the left upper-arm cuff 20L has stenosis, and judges, based on an amount of difference of the each increase-related characteristic value from the normal range, a degree of stenosis of the artery located upstream of the left upper-arm cuff 20L. Similarly, regarding each of the right-upper-arm pulse wave $WB_R$, the left-ankle pulse wave $WA_L$, and the right-ankle pulse wave $WA_R$, the judging means 86 judges, based on each of the increase-related characteristic values of the each pulse wave $WB_R$, $WA_L$, $WA_R$, determined by the increase-related-characteristic-value determining means 84, whether an upstream artery of a portion located upstream of the portion where the corresponding cuff 20R, 18L, 18R is worn has stenosis or not, or what degree of stenosis the upstream artery has.

Figure 8:
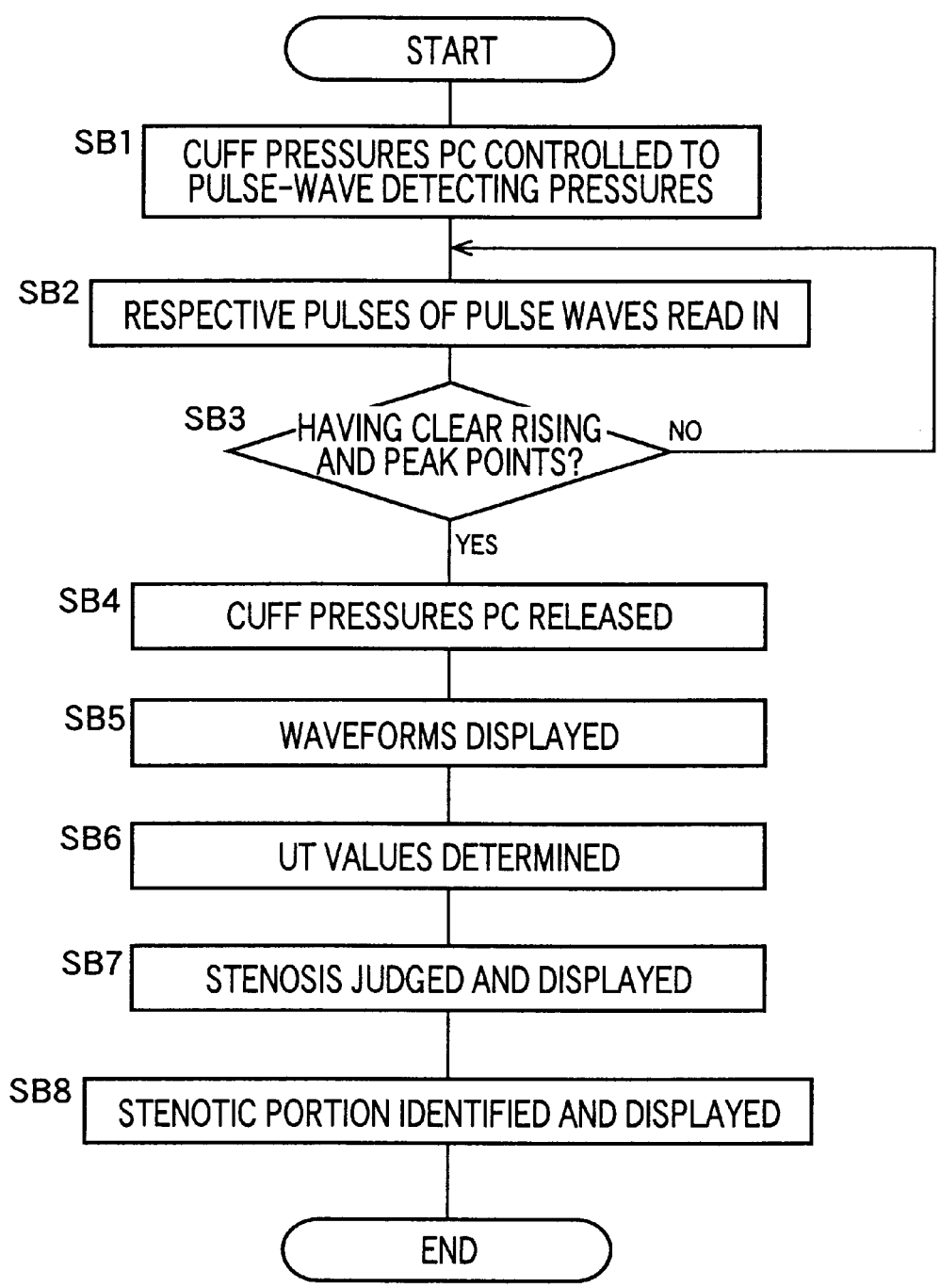
FIG. 8 is a flow chart representing the essential control functions of the CPU, shown in the diagrammatic view of FIG. 7.

FIG. 8 shows a flow chart representing the essential control functions of the CPU 48, shown in the diagrammatic view of FIG. 7. First, at SB1 and SB2, the CPU operates in the same manners as those described with respect to SA1 and SA2 shown in FIG. 5. In short, at SB1, the cuff pressures $PC_a$, $PC_b$, $PC_c$, $PC_d$ are controlled to the respective pulse-wave detecting pressures and, at SB2, the CPU reads in one heartbeat-synchronous pulse of the pulse wave detected by each of the four pulse-wave detecting devices 40, 42, 44, 46.

At SB3, the CPU judges whether a waveform of each of the four heartbeat-synchronous pulses read in at SB2 has a clear rising point and a clear peak point. If a negative judgment is made at SB3, the control goes back to SB2. Thus, the CPU repetitively reads in respective pulses of the four pulse waves till a positive judgment is made at SB3.

If a positive judgment is made at SB3, the control goes to SB4 to release the cuff pressures $PC_a$, $PC_b$, $PC_c$, $PC_d$ in the same manner as that employed at SA10 of FIG. 5. Then, the control goes to SB5 corresponding to the pulse-wave displaying means 82. At SB5, the CPU operates the display device 54 to display the respective waveforms of the respective heartbeat-synchronous pulses of the four pulse waves, read in at SB2, for which the positive judgment had been made at SB3. In the flow chart of FIG. 8, SB3 and SB5 correspond to the pulse-wave displaying means 82.

Subsequently, at SB6, the CPU determines a third UT value (i.e., third stenosis-related information) of the heartbeat-synchronous pulse of the left-upper-arm pulse wave $WB_L$, a fourth UT value (i.e., fourth stenosis-related information) of the heartbeat-synchronous pulse of the right-upper-arm pulse wave $WB_R$, a first UT value (i.e., first stenosis-related information) of the heartbeat-synchronous pulse of the left-ankle pulse wave $WA_L$, and a second UT value (i.e., second stenosis-related information) of the heartbeat-synchronous pulse of the right-ankle pulse wave $WA_R$. For those respective heartbeat-synchronous pulses of the four pulse waves, read in at SB2, the positive judgment had been made at SB3. In the flow chart of FIG. 8, SB3 and SB6 correspond to the increase-related-characteristic-value determining means 84.

Then, the control goes to SB7 and SB8 corresponding to the stenosis judging means 86. At SB7, the CPU judges, based on the UT value of each one of the first to fourth pulse waves, determined at SB6, whether a corresponding one of the first to fourth arteries has stenosis. More specifically described, if the UT value of each one of the first to fourth pulse waves, determined at SB6, falls within a corresponding one of respective normal ranges predetermined for the four pulse waves, the CPU judges that one of the first to fourth arteries that corresponds to the each one pulse wave does not have stenosis; and if not, the CPU judges that the one artery has stenosis. Each one of the first to fourth pulse waves is detected from the downstream end of a corresponding one of the first to fourth arteries. In addition, the CPU operates the display device 54 to display the results of those judgments. Subsequently, at SB8, the CPU identifies a stenotic portion of the patient based on the presence or absence of stenosis in each of the first to fourth arteries, judged at SB7, and the relationship shown in Table 1, and operates the display device 54 to display the identified stenotic portion.

In the embodiment employing the flow chart shown in FIG. 8, at SB6 (the increase-related-characteristic-value determining means 84), the CPU determines, based on the shape of the pulse wave detected by each of the pulse-wave detecting devices 40, 42, 44, 46, the UT value that changes in relation with stenosis of the artery located upstream of the portion where the each pulse-wave detecting device is worn. And, at SB7 and SB8 (the stenosis judging means 86), the CPU makes, based on the thus determined UT value, a judgment about the stenosis of the artery located upstream of the portion where the each pulse-wave detecting device 40, 42, 44, 46 is worn, and identifies the stenotic portion of the patient based on the presence or absence of stenosis of each of the four arteries.

In addition, in the embodiment employing the flow chart shown in FIG. 8, at SB3 and SB6 (the increase-related-characteristic-value determining means 84), the CPU selects, from the respective heartbeat-synchronous pulses of the pulse wave detected by each of the pulse-wave detecting devices 40, 42, 44, 46, one heartbeat-synchronous pulse whose waveform has a clear rising point and a clear peak point, and determines a UT value of the thus selected pulse. A UT value determined for a pulse whose waveform has a clear rising point and a clear peak point is accurate. And, at SB7 and SB8 (the stenosis judging means 86), the CPU makes, based on the thus determined UT value, a judgment about the stenosis of the artery located upstream of the portion where each cuff 18, 20 is worn. Thus, the present apparatus can make an accurate diagnosis about the stenosis of the artery.

Moreover, in the embodiment employing the flow chart shown in FIG. 8, at SB6 (the increase-related-characteristic-value determining means 84), the CPU determines the first UT value based on the shape of the left-ankle pulse wave $WA_L$ detected by the left-ankle-pulse-wave detecting device 44, and the second UT value based on the shape of the right-ankle pulse wave $WA_R$ detected by the right-ankle-pulse-wave detecting device 46. The first UT value reflects the stenosis of the first artery, and the second UT value reflects the stenosis of the second artery. Therefore, if arteriostenosis occurs to the artery A or D, both the first and second UT values indicate arteriostenosis; if arteriostenosis occurs to the artery E, only the first UT value indicates arteriostenosis; and if arteriostenosis occurs to the artery F, only the second UT value indicates arteriostenosis. Thus, at SB7 and SB8 (the stenosis judging means 86), the CPU can make, based on the first and second UT values, a judgment about stenosis of each of the arteries A, D, E, and F, according to the pre-stored relationship shown in Table 1.

In addition, in the embodiment employing the flow chart shown in FIG. 8, at SB5 (the pulse-wave displaying means 82), the CPU operates the display device 54 to display the respective waveforms of the respective heartbeat-synchronous pulses of the four pulse waves, detected by the pulse-wave detecting devices 40, 42, 44, 46, that have been judged as having the respective clear rising and peak points. Since those waveforms are free of deformation, a medical person can make an accurate diagnosis about the stenosis of each of the respective arteries located upstream of the cuffs 18, 20, based on the shape of a corresponding one of the waveforms. If the person make respective judgments about stenosis of the respective arteries located upstream of the respective portions where the four cuffs 18, 20 are worn, based on the four pulse waves displayed on the display device 54, the person can identify a stenotic portion of the patient based on those judgments.

Figure 9:
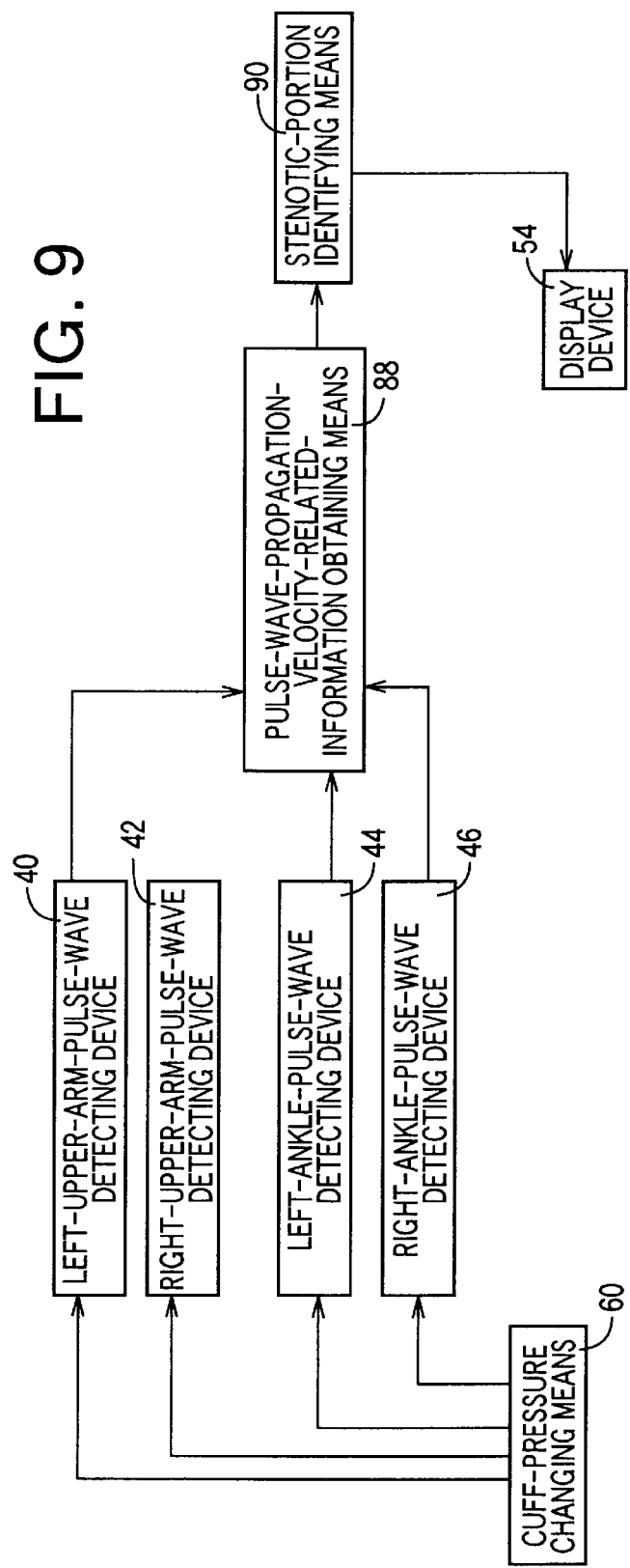
FIG. 9 is a diagrammatic view for explaining control functions of a CPU of a control device of yet another arteriosclerosis examining apparatus as a third embodiment of the present invention.

Next, there will be described yet another embodiment of the present invention. The same reference numerals as used in the above-described first or second embodiment are used to designate the corresponding elements of the present embodiment, and the description thereof is omitted. FIG. 9 shows control functions of the CPU 48 that may additionally be employed in each of the arteriosclerosis examining apparatuses shown in FIGS. 2 and 7.

A pulse-wave-propagation-velocity-related-information obtaining means 88 determines a prescribed point (e.g., a peak point or a rising point) of a heartbeat-synchronous pulse of the left-ankle pulse wave $WA_L$ detected by the left-ankle-pulse-wave detecting device 44 functioning as a first-pulse-wave detecting device, and a prescribed point (e.g., a peak point or a rising point) of a corresponding heartbeat-synchronous pulse of the left-upper-arm pulse wave $WB_L$ detected by the left-upper-arm-pulse-wave detecting device 40 functioning as a third-pulse-wave detecting device. In addition, the information obtaining means 88 determines, as a first pulse-wave propagation time DT1, a time difference between a time of occurrence of the prescribed point of the left-ankle pulse wave $WA_L$ and a time of occurrence of the corresponding prescribed point of the left-upper-arm pulse wave $WB_L$. Moreover, the information obtaining means 88 determines a first pulse-wave propagation velocity PWV1, based on the thus determined first pulse-wave propagation time DT1, according to the following Expression 1 pre-stored in the ROM 50:

$$PWV1=L/DT1 \qquad \text{(Expression 1)}$$

In Expression 1, symbol, L, indicates a difference between a distance between the patient's heart and the portion where the left upper-arm cuff 20L is worn, and a distance between the patient's heart and the portion where the left-ankle cuff 18L is worn, and is equal to a predetermined value.

Similarly, the information obtaining means 88 determines, as a second pulse-wave propagation time DT2, a time difference between a time of occurrence of a prescribed point of a heartbeat-synchronous pulse of the right-ankle pulse wave $WA_R$ detected by the right-ankle-pulse-wave detecting device 46 functioning as a second-pulse-wave detecting device, and a time of occurrence of a prescribed point of a corresponding heartbeat-synchronous pulse of the left-upper-arm pulse wave $WB_L$ detected by the left-upper-arm-pulse-wave detecting device 40. Moreover, the information obtaining means 88 determines a second pulse-wave propagation velocity PWV2, based on the thus determined second pulse-wave propagation time DT2, according to the following Expression 2 pre-stored in the ROM 50:

$$PWV2=L/DT2 \qquad \text{(Expression 2)}$$

A stenotic-portion identifying means 90 determines an information comparison value by comparing first pulse-wave-propagation-velocity-related information (i.e., the first pulse-wave propagation time DT1 or the first pulse-wave propagation velocity PWV1) and second pulse-wave-propagation-velocity-related information (i.e., the second pulse-wave propagation time DT2 or the second pulse-wave propagation velocity PWV2), obtained by the information obtaining means 88, with each other, and more accurately identifies, based on the thus determined information comparison value, a stenotic portion of the first or second artery whose stenosis is identified by the above-described stenosis judging means 68, 86. Here, the information comparison value is defined as a value indicating a degree of difference between the first and second pieces of pulse-wave-propagation-velocity-related information, and may be the difference itself between of the two pieces of information or a ratio of one of the two pieces of information to the other.

The reason why a stenotic portion can be identified based on the information comparison value will be explained, below, using pulse-wave propagation velocity PWV as a sort of pulse-wave-propagation-velocity-related information. If a patient has arteriostenosis, patient's blood pressure lowers on a downstream side of the stenotic portion. Meanwhile, pulse-wave-propagation velocity PWV changes with blood pressure. Therefore, if a patient has arteriostenosis, patient's pulse-wave-propagation velocity PWV lowers on the downstream side of the stenotic portion. If the above-described artery A or D is stenotic, the first and second pulse-wave-propagation velocities PWV1, PWV2 should be substantially equal to each other, because the respective lengths of the first and second arteries located downstream of the stenotic artery A or D are substantially equal to each other. On the other hand, if the artery E is stenotic, the first pulse-wave-propagation velocity PWV1 lowers because of the disease, and an amount of lowering of the first velocity PWV1 increases as the stenotic portion goes upstream along the artery E. However, the second pulse-wave-propagation velocity PWV2 is not influenced by the disease. Thus, if the artery E is stenotic, the first velocity PWV1 is lower than the second velocity PWV2, and is more and more lower than the second velocity PWV2 as the stenotic portion goes upstream along the artery E. Similarly, if the artery F is stenotic, the second velocity PWV2 lowers because of the disease, and an amount of lowering of the second velocity PWV2 increases as the stenotic portion goes upstream along the artery F. Accordingly, a stenotic portion can be identified in more detail based on the information comparison value.

Figure 10:
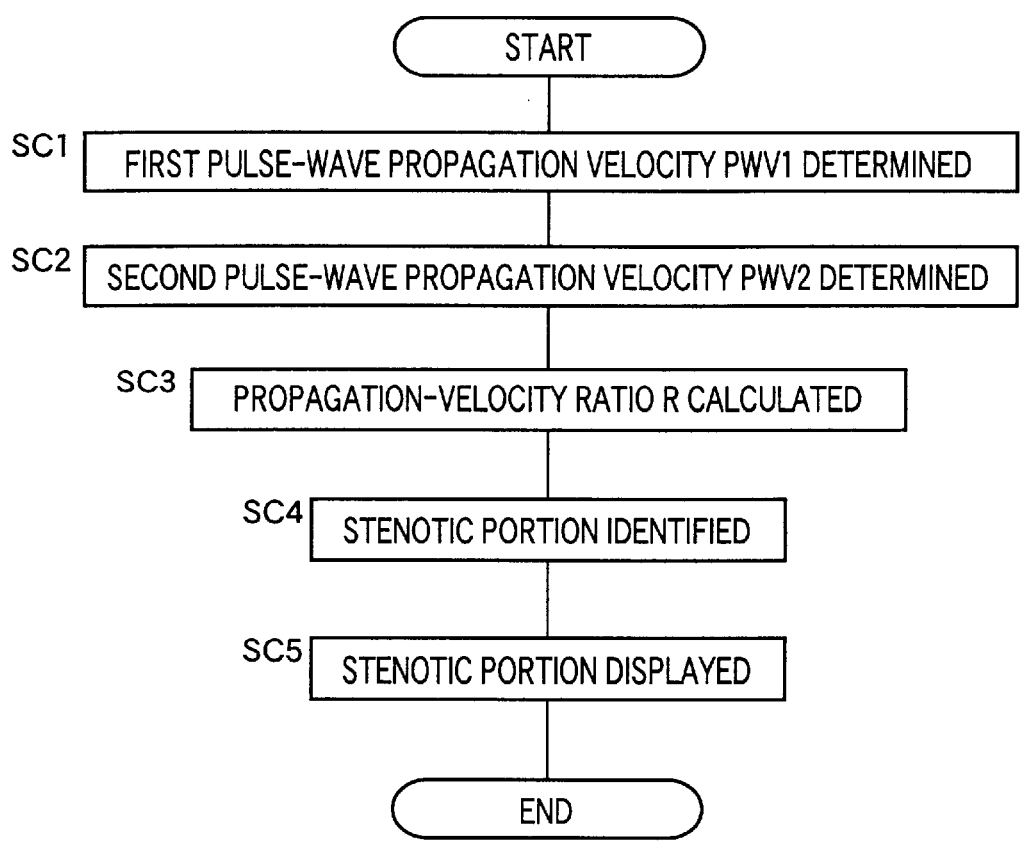
FIG. 10 is a flow chart representing the essential control functions of the CPU, shown in the diagrammatic view of FIG. 9.

FIG. 10 shows a flow chart representing essential control functions of the CPU 48, shown in FIG. 9. This flow chart is executed following the flow chart shown in FIG. 5 or the flow chart shown in FIG. 8.

First, the CPU carries out SC1 and SC2 corresponding to the pulse-wave-propagation-velocity-related-information obtaining means 88. At SC1, the CPU identifies the respective rising points of the respective heartbeat-synchronous pulses of the left-upper-arm pulse wave $WB_L$ and the left-ankle pulse wave $WA_L$, read in at SA6 or SB2, and determines, as a first pulse-wave propagation time DT1, a time difference between respective times of occurrence of the respective rising points thus identified. In addition, the CPU determines a first pulse-wave propagation velocity PWV1 by substituting the thus determined first pulse-wave propagation time DT1 for the above-indicated Expression 1. Then, at SC2, the CPU identifies, like at SC1, the respective rising points of the respective heartbeat-synchronous pulses of the left-upper-arm pulse wave $WB_L$ and the right-ankle pulse wave $WA_R$, read in at SA6 or SB2, and determines, as a second pulse-wave propagation time DT2, a time difference between respective times of occurrence of the respective rising points thus identified. In addition, the CPU determines a second pulse-wave propagation velocity PWV2 by substituting the thus determined second pulse-wave propagation time DT2 for the above-indicated Expression 2.

Subsequently, the control goes to SC3 to SC5 corresponding to the stenotic-portion identifying means 90. At SC3, the CPU divides the first pulse-wave propagation time DT1 determined at SC1, by the second pulse-wave propagation time DT2 determined at SC2, and thereby determines, as a propagation-velocity-related-information comparison value, a propagation-velocity ratio, R (=PWV1/PWV2).

Then, at SC4, the CPU identifies, based on the propagation-velocity ratio R calculated at SC3, a stenotic portion of the patient. More specifically described, if the ratio R falls within a predetermined first range which is greater than 0 and smaller than a predetermined first reference value between 0 and 1, an upstream-side half portion of the artery E is stenotic; if the ratio R falls within a predetermined second range which is greater than the first reference value and smaller than 1, a downstream-side half portion of the artery E is stenotic; if the ratio R falls within a predetermined third range which is greater than a predetermined second reference value considerably greater than 1, an upstream-side half portion of the artery F is stenotic; and if the ratio R falls within a predetermined fourth range which is greater than 1 and smaller than the second reference value, a downstream-side half portion of the artery F is stenotic. At SC5, the CPU operates the display device 54 to display the stenotic portion identified at SC4.

As is apparent from the foregoing description, the pulse-wave propagation velocity PWV determined at SC1 and SC2 (the pulse-wave-propagation-velocity-related-information obtaining means 88) lowers as the stenotic portion goes upstream along the artery for which the velocity PWV is determined. Therefore, the stenotic portion can be identified based on the pulse-wave propagation velocity PWV.

While the present invention has been described in its embodiments by reference to the drawings, the present invention may be otherwise embodiment.

For example, in each of the illustrated embodiments, the four pulse-wave detecting devices 40, 42, 44, 46 are employed. However, it is possible to employ a different number of pulse-wave detecting devices; such as one or two pulse-wave detecting devices only.

Each of the pulse-wave detecting devices may be worn on a portion of a patient other than an upper arm or an ankle. For example, it is possible to employ a pulse-wave detecting device adapted to be worn on a foot articulation in place of an ankle. In addition, it is possible to employ a pulse-wave detecting device which includes a cuff adapted to be worn on a femoral portion and detects a pulse wave from the cuff. In the case where respective pulse waves are detected from a femoral portion and an ankle, it is possible to make a judgment about arteriostenosis of an intermediate portion between the femoral portion and the ankle.

It is possible to employ, as one or more of the pulse-wave detecting devices, a photoelectric-pulse-wave detecting probe for use in oxygen-saturation measurement; a pressure-pulse-wave sensor which is pressed against a prescribed artery such as a radial artery via skin to detect a pressure pulse wave; an impedance-pulse-wave sensor which detects, through electrodes, impedance of, e.g., an arm or a finger; or a photoelectric-pulse-wave sensor which is worn on, e.g., an end portion of a finger to detect pulsation.

At SA12 of FIG. 5, the four pulse waves are displayed, as shown in FIG. 6, such that those pulse waves are arranged in a downward direction. However, it is possible to display the four pulse waves such that those pulse waves overlap one another.

In the above-described third embodiment, the CPU 48 functions as the stenotic-portion identifying means 90 that automatically identifies the stenotic portion of the patient. However, the CPU may be modified to operate the display device 54 to display the first and second pieces of pulse-wave-propagation-velocity-related information. In this case, since a medical person can calculate an information comparison value based on the first and second pieces of pulse-wave-propagation-velocity-related information displayed, the stenotic-portion identifying means 90 may be omitted.

In the above-described third embodiment, the stenotic portion of the patient is identified based on the information comparison value obtained by comparing the first and second pieces of pulse-wave-propagation-velocity-related information with each other. In this case, the influences of individual differences of the patient can be removed by comparing the two pieces of pulse-wave-propagation-velocity-related information simultaneously obtained from the patient, with each other. However, the second piece of pulse-wave-propagation-velocity-related information may be replaced with a standard piece of pulse-wave-propagation-velocity-related information corresponding to, e.g., the age of the patient. In this case, however, the accuracy of diagnosis is decreased as compared with the case where the second piece of pulse-wave-propagation-velocity-related information is used.

In the above-described third embodiment, the left-upper-arm-pulse-wave detecting device 40 is employed as the third-pulse-wave detecting device. However, the portion where the third-pulse-wave detecting device is worn is just required to satisfy the condition that the pulse-wave-propagation-velocity-related-information obtaining means 88 can obtain pulse-wave-propagation-velocity-related information from a portion including an artery located between the junction of the first and second arteries and the portion where the first pulse wave is detected. Therefore, a pulse-wave detecting device which is adapted to be worn on, e.g., a neck portion or a wrist may be employed as the third-pulse-wave detecting device.

While the present invention has been described in detail in its embodiments by reference to the drawings, it is to be understood that the present invention is by no means limited to the details of those embodiments and may be embodied with other changes and improvements that may occur to a person skilled in the art without departing from the spirit and scope of the invention defined in the appended claims.

What is claimed is:

1. An apparatus for examining arteriosclerosis of a living subject, comprising:

a first-pulse-wave detecting device which detects, as a first pulse wave, a pulse wave from a first portion of the subject;

a second-pulse-wave detecting device which detects, as a second pulse wave, the pulse wave from a second portion of the subject that is different from the first portion of the subject;

a stenosis-related-information obtaining means for obtaining, based on a shape of the first pulse wave detected by the first-pulse-wave detecting device, first stenosis-related information that changes in relation with stenosis of a first artery of a third portion of the subject that is located upstream of the first portion of the subject in a direction in which blood flows in the first artery, and obtaining, based on a shape of the second pulse wave detected by the second-pulse-wave detecting device, second stenosis-related information that changes in relation with stenosis of a second artery of a fourth portion of the subject that is located upstream of the second portion of the subject in a direction in which blood flows in the second artery; and a stenosis judging means for making, based on the first stenosis-related information, and the second stenosis-related information, obtained by the stenosis-related-information obtaining means, a judgment about the stenosis of the first artery of the second portion of the subject, a judgment about the stenosis of the second artery of the fourth portion of the subject, and a judgment about a stenosis of a third, common artery that is located upstream of the first and second arteries in a direction in which blood flows in the third artery.

2. An apparatus according to claim 1, further comprising a pulse-wave-propagation-velocity-related information obtaining device which obtains, based on the first pulse wave detected by the first-pulse-wave detecting device, first pulse-wave-progation-velocity-related information that is related to a first velocity at which the pulse wave propagates in a fourth artery of the subject that includes the first artery of the third portion of the subject that is located upstream of the first portion of the subject.

3. An apparatus according to claim 2, wherein the pulse-wave-propagation-velocity-related-information obtaining device obtains, based on the second pulse wave detected by the second-pulse-wave detecting device, second pulse-wave-propagation-velocity-related information that is related to a second velocity at which the pulse wave propagates in a fifth artery of the subject that includes the second artery of the fourth portion of the subject that is located upstream of the second portion of the subject, and wherein the apparatus further comprises a stenotic-portion identifying means for identifying, based on a comparison value obtained by comparing the first pulse-wave-propagation-velocity-related information and the second pulse-wave-propagation-velocity-related information, with each other, a stenotic portion of each of the first and second arteries.

4. An apparatus for examination of arteriosclerosis of a living subject, comprising:

a pulse-wave detecting device which detects, from a portion of the subject, a pulse wave including a plurality of heartbeat-synchronous pulses;

a display device which displays a waveform of at least one heartbeat-synchronous pulse of the pulse wave detected by the pulse-wave detecting device;

a sharpness-degree determining means for determining a degree of sharpness of each of the heartbeat-synchronous pulses of the pulse wave detected by the pulse-wave detecting device;

an average-sharpness-degree calculating means for calculating an average of the respective degrees of sharpness of the heartbeat-synchronous pulses of the pulse wave determined by the sharpness-degree determining means; and a pulse-wave displaying means for operating, when a comparison value obtained by comparing a degree of sharpness of said at least one heartbeat-synchronous pulse of the pulse wave, determined by the sharpness-degree determining means, with the average sharpness degree calculated by the average-sharpness-degree calculating means, falls within a reference range, the display device to display the waveform of said at least one heartbeat-synchronous pulse of the pulse wave.

5. An apparatus for examining arteriosclerosis of a living subject, comprising:

a pulse-wave detecting device which detects a pulse wave from a first portion of the subject;

a stenosis-related-information obtaining means for obtaining, based on a shape of the pulse wave detected by the pulse-wave detecting device, stenosis-related information that changes in relation with stenosis of an artery of a second portion of the subject that is located upstream of the first portion of the subject in a direction in which blood flows in the artery; and a stenosis judging means for making, based on the stenosis-related information obtained by the stenosis-related-information obtaining means, a judgment about the stenosis of the artery of the second portion of the subject, wherein the stenosis-related-information obtaining means comprises:

a sharpness-degree determining means for determining a degree of sharpness of each of a plurality of heartbeat-synchronous pulses of the pulse wave detected by the pulse-wave detecting device; and an average-sharpness-degree calculating means for calculating an average of the respective degrees of sharpness of the heartbeat-synchronous pulses of the pulse wave determined by the sharpness-degree determining means, and wherein the stenosis judging means makes the judgment about the stenosis of the artery of the second portion of the subject, based on a degree of sharpness of at least one heartbeat-synchronous pulse of the pulse wave determined by the sharpness-degree determining means, when a comparison value which is obtained by comparing the degree of sharpness of said at least one heartbeat-synchronous pulse, with the average sharpness degree calculated by the average-sharpness-degree calculating means, falls within a reference range.

* * * * *